US 11,179,490 B2

(12) United States Patent
Clack et al.

(10) Patent No.: US 11,179,490 B2
(45) Date of Patent: Nov. 23, 2021

(54) PROCESS FOR ELECTRO-HYDRODYNAMICALLY ENHANCED DESTRUCTION OF CHEMICAL AIR CONTAMINANTS AND AIRBORNE INACTIVATION OF BIOLOGICAL AGENTS

(71) Applicant: THE REGENTS OF THE UNIVERSITY OF MICHIGAN, Ann Arbor, MI (US)

(72) Inventors: Herek L. Clack, Ann Arbor, MI (US); Krista R. Wigginton, Ann Arbor, MI (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 254 days.

(21) Appl. No.: 15/572,461

(22) PCT Filed: May 6, 2016

(86) PCT No.: PCT/US2016/031163
§ 371 (c)(1),
(2) Date: Nov. 7, 2017

(87) PCT Pub. No.: WO2016/179477
PCT Pub. Date: Nov. 10, 2016

(65) Prior Publication Data
US 2018/0117209 A1    May 3, 2018

Related U.S. Application Data

(60) Provisional application No. 62/158,131, filed on May 7, 2015.

(51) Int. Cl.
*A61L 9/22*    (2006.01)
*H05H 1/48*    (2006.01)
(Continued)

(52) U.S. Cl.
CPC .............. *A61L 9/22* (2013.01); *B01D 53/323* (2013.01); *B03C 3/41* (2013.01); *F24F 3/16* (2013.01);
(Continued)

(58) Field of Classification Search
CPC ..... A61L 9/22; A61L 2209/16; B01D 53/323; B01D 2259/818; B01D 2258/06;
(Continued)

(56) References Cited

U.S. PATENT DOCUMENTS 6,163,098 A    12/2000 Taylor et al.
6,245,126 B1   6/2001 Feldman et al.
(Continued)

FOREIGN PATENT DOCUMENTS

GN    101920032 A    12/2010

OTHER PUBLICATIONS

International Search Report and Written Opinion of the International Searching Authority issued in PCT/US2016/031163, dated Aug. 16, 2016; ISA/KR.
(Continued)

*Primary Examiner* — Regina M Yoo
(74) *Attorney, Agent, or Firm* — Harness, Dickey & Pierce, P.L.C.

(57) ABSTRACT

A method and apparatus for electro-hydrodynamic destruction of an aerosol. The method includes receiving air having large aerosols, greater than about 1 micron, and small aerosols, smaller than about 1 micron, and entraining the large aerosols and small aerosols within an airflow. The airflow is directed to an electric field, which causes the large aerosols to react with the electric field to accumulate an electric charge resulting in extraction of the large aerosols from the airflow. The airflow is also directed to a non-thermal plasma such that the small aerosols remain entrained (Continued)

in the airflow and are subject to electro-hydrodynamic (EHD) phenomena. The non-thermal plasma outputs at least one of radicals, excited species, and ionized atoms and molecules capable of reacting with the small aerosols to result in physical and/or chemical destruction of the small aerosols.

2 Claims, 2 Drawing Sheets

(51) Int. Cl.
*B01D 53/32* (2006.01)
*B03C 3/41* (2006.01)
*F24F 3/16* (2021.01)
*F24F 8/30* (2021.01)
*H05H 1/24* (2006.01)

(52) U.S. Cl.
CPC ............ *H05H 1/48* (2013.01); *A61L 2209/16* (2013.01); *B01D 2257/91* (2013.01); *B01D 2258/06* (2013.01); *B01D 2259/818* (2013.01); *B03C 2201/04* (2013.01); *F24F 8/30* (2021.01); *H05H 1/475* (2021.05); *H05H 2240/10* (2013.01); *H05H 2240/20* (2013.01)

(58) Field of Classification Search
CPC .............................. B01D 2257/91; F24F 3/16; F24F 2003/1682; B03C 3/41; B03C 2201/04; H05H 1/48; H05H 2240/20; H05H 2240/10; H05H 2001/486; F15D 1/02
See application file for complete search history.

(56) References Cited

U.S. PATENT DOCUMENTS

| | | | |
|---|---|---|---|
| 6,544,485 B1 | 4/2003 | Taylor | |
| 6,562,386 B2* | 5/2003 | Ruan | A23L 3/26 204/164 |
| 6,811,757 B2* | 11/2004 | Niv | H05H 1/2406 204/164 |
| 6,957,528 B1* | 10/2005 | Cho | F01N 3/206 60/275 |
| 7,060,231 B2* | 6/2006 | Cho | B01D 53/323 204/177 |
| 7,192,553 B2* | 3/2007 | Crowe | A61L 2/14 422/23 |
| 8,398,923 B2 | 3/2013 | Mole | |
| 8,529,830 B2* | 9/2013 | Zhou | A61L 9/22 422/4 |
| 8,771,600 B2 | 7/2014 | Ray | |
| 9,603,870 B2* | 3/2017 | Mortenson | A61P 25/16 |
| 10,449,217 B2* | 10/2019 | Mortenson | B22F 9/00 |
| 2002/0153241 A1* | 10/2002 | Niv | H05H 1/2406 204/164 |
| 2007/0266702 A1* | 11/2007 | Cotton | F01N 3/01 60/298 |
| 2008/0063577 A1 | 3/2008 | Crowe et al. | |
| 2011/0229376 A1 | 9/2011 | Ray | |
| 2012/0269677 A1 | 10/2012 | Zhou et al. | |
| 2013/0259903 A1* | 10/2013 | Mortenson | A61P 25/16 424/400 |
| 2015/0038584 A1 | 2/2015 | Fridman et al. | |

OTHER PUBLICATIONS

Supplementary European Search Report issued in EP16790147.9, dated Nov. 2, 2018.
Roth, Reece J., et al. "The One Atmosphere Uniform Glow Discharge Plasma (OAUGDP)—A Platform Technology for the 21st Century," IEEE Transactions on Plasma Science, vol. 35, No. 2 (Apr. 2007), pp. 233-250.
Melcher, J R. and G.I. Taylor, Electrohydrodynamics: A Review of the Role of Interfacial Shear Stresses. Annual Review of Fluid Mechanics, 1969. 1: p. 111-146.
Fylladitakis, E.D., M.P. Theodoridis, and A.X. Moronis, Review on the History, Research, and Applications of Electrohydrodynamics. IEEE Transactions on Plasma Science, 2014. 42(2): p. 358-375.
Laohalertdecha, S., P. Naphon, and S. Wongwises, A review of electrohydrodynamic enhancement of heat transfer. Renewable and Sustainable Energy Reviews, 2007. 11(5): p. 858-876.
IEEE-DEIS-EHD Technical Committee, Recommended International Standard For Dimensionless Parameters Used in Electrohydrodynamics. IEEE Transactions on Dielectrics and Electrical Insulation, 2003. 19(1): p. 3-6.

* cited by examiner

PROCESS FOR ELECTRO-HYDRODYNAMICALLY ENHANCED DESTRUCTION OF CHEMICAL AIR CONTAMINANTS AND AIRBORNE INACTIVATION OF BIOLOGICAL AGENTS

CROSS-REFERENCE TO RELATED APPLICATIONS

This application is a U.S. National Phase Application under 35 U.S.C. 371 of International Application No. PCT/US2016/031163 filed on May 6, 2016 and published in English as WO 2016/179477 A1 on Nov. 10, 2016. This application claims the benefit of U.S. Provisional Application No. 62/158,131, filed on May 7, 2015. The entire disclosures of the above applications are incorporated herein by reference.

FIELD

The present disclosure relates to the electro-hydrodynamically (EHD) enhanced destruction of chemical air contaminants and airborne inactivation of biological agents.

BACKGROUND AND SUMMARY

This section provides background information related to the present disclosure which is not necessarily prior art. This section provides a general summary of the disclosure, and is not a comprehensive disclosure of its full scope or all of its features.

Increasing public alarm over viral outbreaks has heightened the public's interest in how pathogens are transmitted and what health-protective measures can be used against transmission. More generally, chemical contaminants and biological pathogens in air likely raise the level of public concern because they are unseen, thereby increasing public concern when health impacts are severe or when sources are diffuse, unidentifiable and/or uncontrolled. Approximately 75% of acute illnesses in the developed world are respiratory, and nearly 80% of these illnesses are caused by viruses which are often transmitted in indoor environments. A stark example of disease transmission within indoor environments is the 2003 SARS coronavirus outbreak when fecal matter-contaminated aerosols conveyed through the ventilation system were found to be responsible for a large cluster of SARS infections concentrated in the Amoy Gardens high-rise apartment block in Hong Kong. Indoor air quality will continue to increase in importance as global populations continue to grow, city populations continue to swell from rural-to-urban migration patterns, and residential and commercial building occupant densities continue to rise as a result.

According to the principles of the present teachings, prevention of the transmission of viruses and bacteria through centralized HVAC systems without need for a particulate filter is provided, thereby preventing contamination of indoor environments by external biological agents. In some embodiments, the present teachings employ one or more electrical discharges that impose an electric field which concurrently charges and removes from the air stream infectious aerosols that are of larger diameter, while also inducing electro-hydrodynamic phenomena to focus air streams and the infectious aerosols of smaller diameter contained within them in the regions of highest potential for pathogen destruction and provide a means for dynamic response to different pathogens, air flow rates, and general air conditions, and mitigation of undesirable gaseous species. This provides the potential for use in central HVAC systems without the energy penalty associated with particulate filters and avoiding the resulting lower pressure at which any downstream environment must be held when using particulate filters.

The present teachings may find utility in a wide variety of applications, including but not limited to commercial HVAC systems, sterile room contaminant control, commercial aircraft cabin environmental control, bio-security, confined animal operations, and the like. The present teachings achieve many benefits, including but not limited to being filterless, reduced operating costs compared to particulate filters, being tunable, and the ability to achieve EPA recommendations not achievable by today's technology.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 3A:
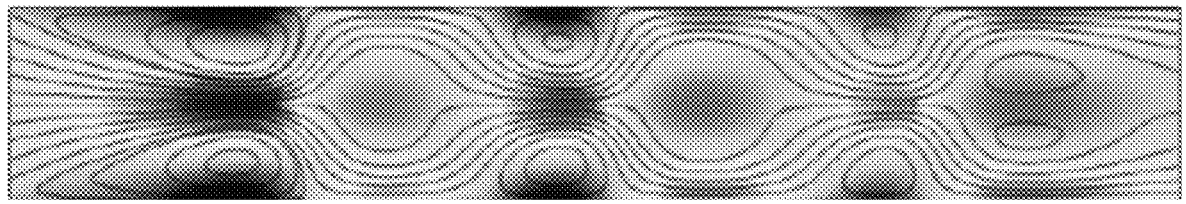
Figure 3B:
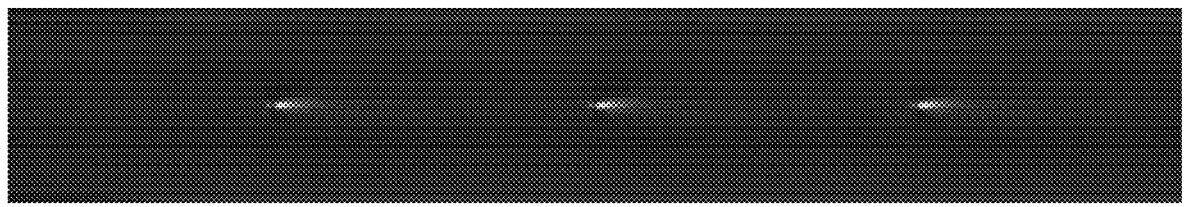
Figure 3C:
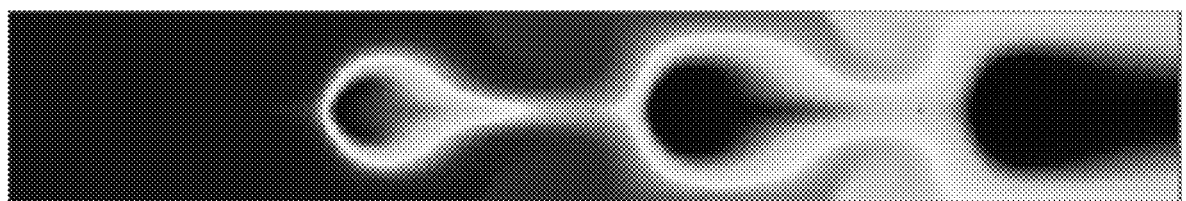
Figure 3D:
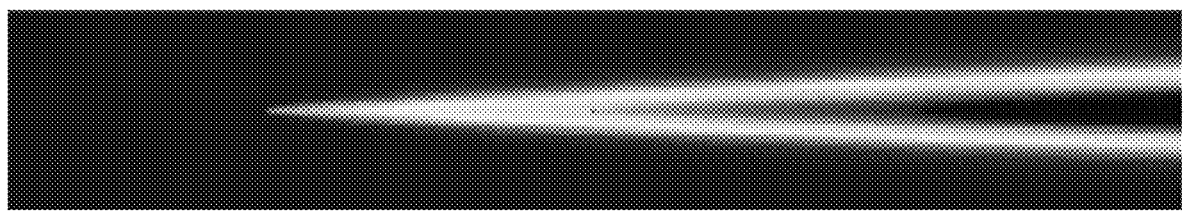

FIGS. 3A-3D are results from 2-D numerical simulations of a representative air flow during treatment within such a system. Shown is a 2-D channel through which the air flows (0.1 m/s, entering from the left) in which three wire electrical discharge electrodes (0.5 cm diameter) are positioned along the centerline. FIGS. 3A and 3B show how the air flow patterns differ in the channel with (3A) and without (3B) a voltage applied to the wire discharge electrodes. In both figures, fluid streamlines represent flow direction and shading represents velocity magnitude, with greater variations in velocity magnitude and greater divergence in flow direction shown in FIG. 3A (−70 kV applied voltage) than in FIG. 3B (0 kV) In FIGS. 3C and 3D, shading represents contaminant concentration. For the same conditions as FIGS. 3A and 3B, destruction of airborne contaminants due to destruction by excited species comprising the non-thermal plasma is greater (67.3%) under the influence of electro-hydrodynamic enhancement (FIG. 3C) than would occur from the plasma without the electro-hydrodynamic enhancement (34.1%, FIG. 3D). (Reaction rate=1000 $m^6/mol^2$).

Corresponding reference numerals indicate corresponding parts throughout the several views of the drawings.

DETAILED DESCRIPTION

Example embodiments will now be described more fully with reference to the accompanying drawings. Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

As discussed herein, chemical contaminants and biological pathogens in air raise public concern over viral outbreaks and serious health effects. Therefore, effective and economical health-protective methods to achieve inactivation of these airborne pathogens are highly desirable.

In some embodiments of the present teachings, the electric field accompanying an electrical discharge or non-thermal plasma (NTP) is used to provide several beneficial effects. For example, according to some embodiments, larger aerosols, such as those having a particle diameter greater than about 1 µm, accumulate a higher electrical charge that causes them to be more rapidly extracted from the air stream than smaller aerosols. Smaller aerosols, such as those having a particle diameter less than about 1 µm, remain entrained in the air stream as it interacts with strong electric fields and becomes subject to electro-hydrodynamic (EHD) phenomena. The smaller-sized infectious aerosols are carried along with the EHD-influenced air flow into, or near to, regions in which non-thermal plasmas exist. For purposes of the present discussion, aerosols will be used generally to indicate fine solid particles or liquid droplets, including, but not limited to, haze, dust, particulate air pollutants, smoke, fume, viruses, pathogens, bacteria, pollen, grain, spores, airborne contaminant, biological agent, and the like. Large aerosols are generally regarded as those aerosols having a particle diameter greater than about 1 micron (µm) and small aerosols are generally regarded as those aerosols having a particle diameter smaller than about 1 micron (µm).

Plasmas consist of radicals, excited species, and ionized atoms and molecules, all of which are highly reactive. The chemical breakdown catalyzed by NTPs has been shown to effectively destroy a variety of chemical compounds through chemical reaction pathways similar to those inherent to combustion-driven chemical oxidation, a form of thermal plasma. In the context of biological pathogens, radicals and excited species are thought to chemically attack the outer membrane or capsid, whereby the resulting damage leads to a loss in structural integrity. The use of EHD phenomena to direct the air flow and the infectious aerosols entrained within it toward plasma-containing regions having high concentrations of reactive species increases the likelihood of complete inactivation of the pathogen by chemical, physical, and radiological processes.

Figure 1:
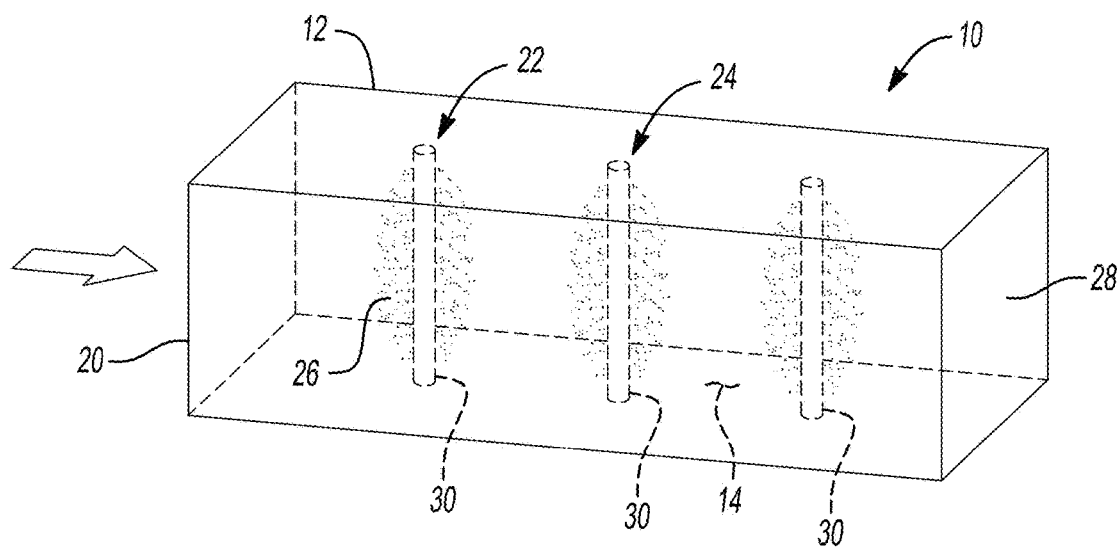
FIG. 1 is a perspective view of an electro-hydrodynamic for destruction of chemical and biological air contaminants system according to the principles of the present teachings.
Figure 2:
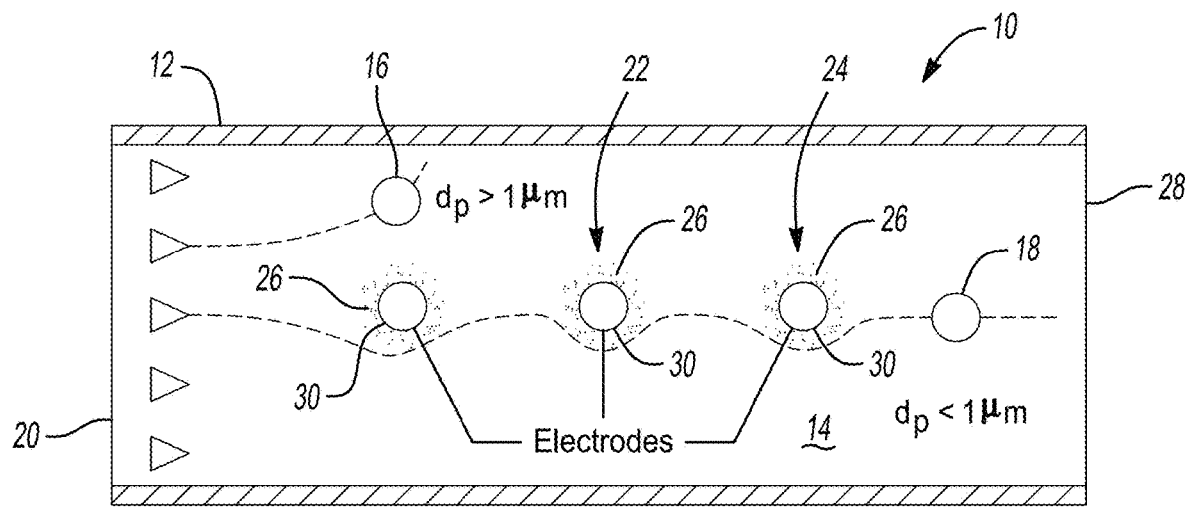
FIG. 2 is a schematic top view of the electro-hydrodynamic system.

FIGS. 1 and 2 schematically illustrates how these different aerosol behaviors would be manifested in EHD-driven fluid flows in a wire-plate configuration according to some embodiments. With particular reference to FIGS. 1 and 2, in some embodiments, an electro-hydrodynamic system 10 is provided for destruction of large aerosols greater than about 1 micron and small aerosols smaller than about 1 micron. The electro-hydrodynamic system 10 can comprise an airflow handling system 12 having an interior volume 14 for receiving an airstream therethrough. The airstream can comprise large aerosols 16 and small aerosols 18. The airflow handling system 12 can include an air inlet 20 receiving the air having the large aerosols 16 and the small aerosols 18. The air handling system 12 entrains the large aerosols 16 and the small aerosols 18 in the air stream, at least initially. As the airstream passes through the airflow handling system 12, an electric field system 22 outputs an electric field capable of extracting the large aerosols 16 from the air stream and exerts electro-hydrodynamic (EHD) phenomena upon the airstream and the small aerosols 18 contained within it. A non-thermal plasma system 24 is provided that outputs a non-thermal plasma 26 such that at least one of radicals, excited species, and ionized atoms and molecules chemically react with the small aerosols 18 to result in physical and/or chemical destruction of the small aerosols 18.

In some embodiments, the air pressure upstream of the electric field system 22 and the non-thermal plasma system 24, such as near the inlet 20, is equal to an air pressure downstream of the electric field system 22 and the non-thermal plasma system 24, such as near an outlet 28.

In some embodiments, it should be understood that the electric field system 22 and the non-thermal plasma system 24 can be configured as an integral system such electrodes are used to output both the electric field and created the non-thermal plasma 26. Conversely, it should be understood that the electric field system 22 and the non-thermal plasma system 24 can be discrete systems tunable to achieve a desired performance. Therefore, the present teachings should not be regarded as requiring an integral or a discrete configuration unless otherwise claimed.

In some embodiments, the electric field system 22 and the non-thermal plasma system 24 can comprise a wire-plate non-thermal plasma system outputting the electric field and the non-thermal plasma 26. The wire-plate non-thermal plasma system can comprise a plurality of wire electrodes 30. In some embodiments, the spacing of the wire electrodes can be in the range of about 0.75 m to about 0.25 m. However, alternative wire sizing, spacing, and configuration orientations are regarded as being part of the present disclosure.

EHD phenomena in a wire-plate configuration have the effect of focusing the fluid flow, and the smaller-sized aerosols entrained within it, in the regions of stable plasma around the wire electrodes. In this way, wire-plate NTP configurations leverage EHD phenomena to expose entrained sub-micron aerosols to the relatively small regions of stable plasma around the wire electrodes, maximizing their exposure to destructive radical species that cause physical, chemical, and genetic damage sufficient to leave the pathogen non-infective.

In addition, the unobstructed flow path traversed by the airstream imposes virtually no velocity head loss (pressure drop) as compared to HEPA filters or even configurations involving a packed bed of material supporting the electrical discharge. There is also evidence that design optimization of wire-plate configurations could yield improved performance: in recent simulations, it has been found that decreasing wire electrode spacing from 0.75 to 0.25 m increased airborne pathogen inactivation by 25% while maintaining constant current density. Therefore, it should be understood that electrode position, orientation, number and scale can, individually or collectively, yield improved performance.

The present teachings can be contrasted against current ultraviolet germicidal irradiation (UVGI) technologies. UVGI uses UV energy to impart damage to airborne pathogens. It is in wide use for surface disinfection; however, its efficacy for true airborne disinfection is unproven at the moment. A distinguishing feature of the present teachings, compared to conventional UVGI methodology, is the use of the electro-hydrodynamic (EHD) phenomena to a) extract larger aerosols from the air stream without the need for an air filter and b) maximize the efficiency of pathogen inactivation by conveying smaller aerosols into contact with destructive reactive species capable of rendering the pathogen non-infective.

Supporting data includes simulation that provides proof-of-concept and more effective inactivation of airborne pathogens than traditional disinfecting technologies. In addition, the present teachings enable filterless filtration, minimizing the cost for filter purchases. Because there are no filters in the system, the operating costs are expected to be lower than operations with filters.

In both NTPs and thermal plasmas (i.e., combustion), the concentration of excited species decreases with distance from the source. In thermal plasmas, the concentration of excited species is closely linked to the thermodynamic gas temperature, with the highest-temperature regions of the flame providing the greatest potential for chemical destruction. NTPs are driven by the electrical breakdown of a gas due to the high electric potential gradient that occurs in the vicinity of an electrical discharge electrode. A distinguishing feature of the present teachings is how it leverages both the size-dependent extraction of aerosols from the air stream and the influence of EHD phenomena to prevent transmission of infectious aerosols: Larger infectious aerosols are extracted from the flow as a result of their greater acquired electrical charge and the forces exerted on them in the presence of an electric field. Smaller infectious aerosols remain entrained in the EHD-influenced air stream carried to, or near to, the region of non-thermal plasma where the highest concentrations of radicals, excited species, and ionized atoms and molecules exist. In this way, viruses, bacteria, or infectious aerosols containing viruses and bacteria, receive higher doses of radicals, excited species, and ionized atoms and molecules, ultimately facilitating more complete inactivation. FIGS. 3A-3D presents numerical modeling simulations that illustrate the effect of EHD phenomena on fluid patterns (as compared to a conventional, charge-neutral fluid flow), as well as the influence of EHD phenomena on chemical reactions between contaminants in the air flow and excited species produced by the three wire discharge electrodes (as compared to a conventional, charge-neutral fluid flow).

Comparisons to Related Technologies

The most commonly used protection against airborne pathogen transmission is the personal face mask. Filtration of this sort, however, is problematic within heating, ventilation, and air conditioning (HVAC) systems because of the high energy penalties incurred when using low-permeability filtration media. To capture micron-sized and smaller bio-aerosols such as viruses and bacteria, very low permeability particulate matter (PM) filters, such as high efficiency particulate air (HEPA) filters, can be used in face masks but are generally considered to be impractical or ineffective for use in portable room air cleaners and HVAC systems. The U.S. EPA advises that moderately permeable PM filters that provide lower PM removal efficiencies but higher clean air delivery rates (CADRs) may yield indoor air quality that is equivalent to, and less expensive to achieve than, using higher performing but more expensive HEPA filters. While such trade-offs may be reasonable for maintaining acceptable concentrations of biologically inactive PM, viruses are known to be infective at doses as low as 1-10 infective units. Therefore, compared to biologically inactive PM, protective measures against infection from bio-aerosols requires a higher level of performance.

Within HVAC systems, current technologies used for preventing airborne pathogen transmission include UV germicidal irradiation (UVGI) or photo-catalytic oxidation (PCO), both of which use UV energy to impart damage to airborne pathogens. In the case of PCO, the presence of the catalyst multiplies the effectiveness of the UV irradiation by producing radicals and excited species, most effectively in the presence of water vapor. However, PCO can be more expensive due to the cost of the catalyst and optimal configuration of the UV source can be challenging when the objectives are uniform irradiation and high ratios of catalyst surface area to volumetric flow rate (space velocity). Over time the effectiveness of the catalyst will decrease due to deactivation and accumulated deposits.

In the case of UVGI, the emitted UV-C radiation is most often used to impart direct biological damage, similar to solar UV damage to human skin cells. UV irradiation is already in wide use for surface disinfection, where immobilized pathogens can be exposed indefinitely. UVGI for airstream disinfection is an extension of the surface disinfection approach in that a UV source irradiates the upstream face of a PM filter on which airborne pathogens are collected. Thus, the presence of a PM filter to extend UV exposure times and achieve higher UV doses differentiates conventional UVGI from the present technology, which operates without a filter and exposes airborne pathogens to higher doses of excited species via EHD manipulation of the airstream. Some UVGI manufacturers advertise that their products are capable of true airstream disinfection, i.e., inactivation of airborne pathogens suspended within a flowing airstream. The U.S. EPA specifically advises that such claims are unsubstantiated, unlikely to be true, and that there currently is no commonly accepted test procedure for evaluating such performance. One manufacturer's specifications document lists the required UV dose for 90% and 99% inactivation of a variety of viruses and bacteria, providing vendor-approved data to compare against the EPA advisory. American Ultraviolet Company provides a representative product specification table of product-specific UV-C radiant intensities and compares them to the values needed to destroy 90% or 99.9% of more than two dozen organisms. For a UV-C source positioned two to three feet from the disinfection surface, one minute of irradiation provides a dose in the range of 15 000 to 35 000 $\mu$W-s/cm$^2$, an exposure time that is only feasible for surface disinfection applications. If instead one considers one second exposure times to be a more representative timescale for true airborne disinfection, the resulting UV dose (250-580 $\mu$W-s/cm$^2$) is insufficient to meet the 90% destruction for all of the listed organisms. Separate, independent, and peer-reviewed results indicate even less effective destruction efficiency: UV doses of 25-50 mJ/cm$^2$ (25 000-50 000 $\mu$W-s/cm$^2$) resulting from one-minute UV exposures generally achieved less than 50% destruction of influenza A virus.

Operating Principles

Unlike physical filtration alone, non-thermal plasmas (NTPs) can address both transport and infectivity by 1)

electrostatic removal of larger particles (>1 μm) and 2) sterilization of the remaining smaller particles by direct plasma exposure.

NTPs are stable electrical discharges formed when an applied electric field is locally strong enough to sustain the continuous dissociation and ionization of atoms and molecules (electrical breakdown), and local emission of free electrons. In the presence of the locally strong electric field, free electrons are accelerated to speeds sufficient to ionize additional species (charge cascading) as well as initiate chemical decomposition reactions of neutral species. The reactive species produced by NTPs depend on the carrier gas used; in ambient air, NTPs produce a number of reactive species including O., OH—, and OH., species that are orders of magnitude more reactive than ozone ($O_3$) used in consumer-grade ozonation air cleaning technologies.

As discussed herein, NTPs are presently used for surface disinfection where they inactivate biological pathogens on the surfaces of food products, treat skin diseases, and promote post-surgical wound healing. NTPs have also been thoroughly studied as an effective treatment for gaseous pollutants, such as volatile organic compounds and nitrous and sulfurous oxides (NOx and SOx) produced from combustion.

However, the intersection of these two established NTP applications—disinfection of airstreams—can be greatly complicated by the influence of the strong electric fields, separately and collectively, on the aerosol and fluid phase motion. This coupling between fluid dynamics and electrostatics is known as electro-hydrodynamics or EHD. In air, it has been found that NTPs provide bactericidal and virucidal activity analogous to that observed in water: reactive radical and oxidant attack on the bacterial cell membrane or virus capsid, causing damage that leads to loss of structural integrity and eventual cell death (bacteria) or disruption of viral genome injection into cells (viruses). For NTP treatment of bare DNA strands in water, it was previously observed that strand breakage in λDNA (48 502 bp) with a linear correlation observed between applied electrical power and the measured rate constant for double-strand genome breakage.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An electro-hydrodynamic system for destruction of biological pathogen particles, the electro-hydrodynamic system comprising:
    an air handling system having an interior volume configured to receive an airstream therethrough, said airstream entraining an aerosol containing large biological pathogen particles having diameters larger than 1 micrometer and small biological pathogen particles having diameters smaller than 1 micrometer;
    wherein said air handling system comprises an air inlet configured to receive said airstream comprising said aerosol having the large biological pathogen particles and the small biological pathogen particles; and
    an integrally-formed electric field and non-thermal plasma system configured to output an electric field configured to extract the large biological pathogen particles from the airstream and to exert electro-hydrodynamic (EHD) phenomena upon the airstream and the small biological pathogen particles contained within it, the integrally-formed electric field and non-thermal plasma system configured to further output a non-thermal plasma comprising at least one of radicals, excited species, and ionized atoms and molecules, the non-thermal plasma configured to chemically react with the small biological pathogen particles for destruction thereof, the integrally-formed electric field and non-thermal plasma system comprises a wire-plate non-thermal plasma system outputting the electric field and the non-thermal plasma, the wire-plate non-thermal plasma system having a plurality of wire electrodes spaced in the range of 0.25 m to 0.75 m.

2. The electro-hydrodynamic system according to claim 1 wherein an air pressure upstream of the integrally-formed electric field and non-thermal plasma system is equal to an air pressure downstream of the integrally-formed electric field and non-thermal plasma system.

* * * * *